(12) United States Patent
Geddes

(10) Patent No.: US 8,618,505 B2
(45) Date of Patent: Dec. 31, 2013

(54) PLASMONIC ELECTRICITY

(75) Inventor: Chris D. Geddes, Bel-Air, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 294 days.

(21) Appl. No.: 13/119,483

(22) PCT Filed: Sep. 17, 2009

(86) PCT No.: PCT/US2009/057282
§ 371 (c)(1),
(2), (4) Date: Apr. 21, 2011

(87) PCT Pub. No.: WO2010/033677
PCT Pub. Date: Mar. 25, 2010

(65) Prior Publication Data
US 2012/0091349 A1    Apr. 19, 2012

Related U.S. Application Data

(60) Provisional application No. 61/097,782, filed on Sep. 17, 2008.

(51) Int. Cl.
*G21H 3/02*    (2006.01)
(52) U.S. Cl.
USPC ..................................... 250/458.1; 250/459.1
(58) Field of Classification Search
USPC ........................................... 250/458.1, 459.1
See application file for complete search history.

(56) References Cited

U.S. PATENT DOCUMENTS

| | | | |
|---|---|---|---|
| 5,017,009 A | 5/1991 | Schutt et al. | |
| 5,449,918 A | 9/1995 | Krull et al. | |
| 5,841,143 A | 11/1998 | Tuma et al. | |
| 5,866,433 A | 2/1999 | Schalkhammer et al. | |
| 7,095,502 B2 | 8/2006 | Lakowicz et al. | |
| 7,253,452 B2 | 8/2007 | Steckel et al. | |
| 7,348,182 B2 | 3/2008 | Martin et al. | |
| 7,351,590 B2 | 4/2008 | Martin | |
| 7,400,397 B2 | 7/2008 | Lakowicz et al. | |
| 7,648,834 B2 | 1/2010 | Moore | |
| 7,718,445 B2 | 5/2010 | Martin | |
| 7,718,804 B2 | 5/2010 | Geddes et al. | |
| 7,732,215 B2 | 6/2010 | Geddes et al. | |
| 7,939,333 B2 | 5/2011 | Geddes et al. | |
| 8,008,067 B2 | 8/2011 | Geddes et al. | |

(Continued)

FOREIGN PATENT DOCUMENTS

| | | |
|---|---|---|
| WO | WO89/09408 | 10/1989 |
| WO | WO2004/024191 | 3/2004 |

OTHER PUBLICATIONS

Asian et al., Metal-Enhanced Fluorescence from Gold Surfaces: Angular Dependent Emission, 2007, Journal of Fluorescence, vol. 17, pp. 7-13.*

(Continued)

*Primary Examiner* — Christine Sung
(74) *Attorney, Agent, or Firm* — Marianne Fuierer; Moore & Van Allen, PLLC

(57) ABSTRACT

The present invention relates to detection systems and methods that detect fluorescence, luminescence, chemiluminescence or phosphorescence signatures in the form of an electrical signal conducted and emitted from metallic containing surfaces. Thus, the present invention provides for detecting fluorescence digitally and directly without the need for expensive detectors.

19 Claims, 16 Drawing Sheets

(56) References Cited

U.S. PATENT DOCUMENTS

| | | | |
|---|---|---|---|
| 8,034,633 | B2 | 10/2011 | Geddes |
| 8,075,956 | B2 | 12/2011 | Geddes et al. |
| 2003/0228682 | A1 | 12/2003 | Lakowicz et al. |
| 2005/0053974 | A1 | 3/2005 | Lakowicz et al. |
| 2006/0147927 | A1 | 7/2006 | Geddes et al. |
| 2007/0115474 | A1 | 5/2007 | Chaton et al. |
| 2007/0269826 | A1 | 11/2007 | Geddes et al. |
| 2007/0278607 | A1 | 12/2007 | Gruhlke et al. |
| 2008/0215122 | A1 | 9/2008 | Geddes et al. |
| 2009/0022766 | A1 | 1/2009 | Geddes et al. |
| 2009/0325199 | A1 | 12/2009 | Geddes et al. |
| 2010/0062545 | A1 | 3/2010 | Geddes et al. |
| 2010/0209937 | A1 | 8/2010 | Geddes et al. |
| 2010/0297016 | A1 | 11/2010 | Geddes et al. |
| 2011/0020946 | A1 | 1/2011 | Geddes |
| 2011/0136154 | A1 | 6/2011 | Geddes |
| 2011/0207236 | A1 | 8/2011 | Geddes |

OTHER PUBLICATIONS

Aslan, K.; Geddes, C. D., Microwave-accelerated metal-enhanced fluorescence: Platform technology for ultrafast and ultrabright assays, *Analytical Chemistry* 2005, 77, 8057-8067.

Aslan, K.; Zhang, Y.; Hibbs, S.; Baillie, L.; Previte, M. J.; Geddes, C. D., Microwave-accelerated metal-enhanced fluorescence: application to detection of genomic and exosporium anthrax DNA in < 30 seconds, *Analyst* 2007, 132, 1130-1138.

Aslan, K., Leonenko, Z., Lakowicz. J.R., Geddes, C.D., Annealed silver-island films for applications in metal-enhanced fluorescence: Interpretation in terms of radiating plasmons, J. Fluoresc. 2005, 15, 643-654.

Aslan, K.; Gryczynski, I.; Malicka, J.; Matveeva, E.; Lakowicz, J. R.; Geddes, C. D, Metal-enhanced fluorescence: an emerging tool in biotechnology, *Current Opinion in Biotechnology* 2005, 16, 55-62.

Aslan, K.; Lakowicz, J. R.; Szmacinski, H.; Geddes, C. D., Enhanced ratiometric pH sensing using SNAFL-2 on silver island films: Metal-enhanced fluorescence sensing, *Journal of Fluorescence* 2005, 15, 37-40.

Aslan, K.; Geddes, C. D., Microwave-accelerated Metal-enhanced Fluorescence (MAMEF): Application to ultra fast and sensitive clinical assays, *Journal of Fluorescence* 2006, 16, 3-8.

Aslan, K.; Holley, P.; Geddes, C. D., Microwave-Accelerated Metal-Enhanced Fluorescence (MAMEF) with silver colloids in 96-well plates: Application to ultra fast and sensitive immunoassays, High Throughput Screening and drug discovery, *Journal of Immunological Methods* 2006, 312, 137-147.

Collings, F. B.; Vaidya, V. S. : Novel technologies for the discovery and quantitation of biomarkers of toxicity, *Toxicology* 2008, 245, 167-174.

Enander, K.; Choulier, L.; Olsson, A. L.; Yushchenko, D. A.; Kanmert, D.; Klymchenko, A. S.; Demchenko, A. P.; Mely, Y.; Altschuh, D., A peptide-based, ratiometric biosensor construct for direct fluorescence detection of a protein analyte, *Bioconjug Chem* 2008.

Geddes, C. D.; Lakowicz, J. R., Metal-enhanced fluorescence, *Journal of Fluorescence* 2002, 12, 121-129.

Gould, R. K.; Coakley, W. T.; Grundy, M. A., Upper Sound Pressure Limits on Particle Concentration in Fields of Ultrasonic Standing-Wave At Megahertz Frequencies, *Ultrasonics* 1992, 30, 239-244.

Lofas, S.; Malmqvist, M.; Ronnberg, I.; Stenberg, E.; Liedberg, B.; Lundstrom, I., Bioanalysis With Surface-Plasmon Resonance, *Sensors and Actuators B-Chemical* 1991, 5, 79-84.

Matveeva, E.; Malicka, J.; Gryczynski, I.; Gryczynski, Z.; Lakowicz, J. R., Multi-wavelength immunoassays using surface plasmon-coupled emission *Biochem Biophys Res Commun* 2004, 313, 721-726.

Matveeva, E.; Gryczynski, Z.; Gryczynski, I.; Malicka, J.; Lakowicz, J. R., Myoglobin immunoassay utilizing directional surface plasmon-coupled emission, *Analytical Chemistry* 2004, 76, 6287-6292.

Neppiras, E. A., Acoustic Cavitation, *Phys. Rep.* 1980, 61, 159-251.

Suslick, K. S.; Flannigan, D. J., Inside a collapsing bubble: Sonoluminescence and the conditions during cavitation, *Annu Rev Phys Chem* 2008, 59, 659-683.

Schultz, E.; Galland, R.; Du Bouetiez, D.; Flahaut, T.; Planat-Chretien, A.; Lesbre, F.; Hoang, A.; Volland, H.; Perraut, F., A novel fluorescence-based array biosensor: Principle and application to DNA hybridization assays, *Biosens Bioelectron* 2008, 23, 987-994.

Suslick, K. S., Sonochemistry, *Science* 1990, 247, 1439-1445.

Taipa, M. A., Immunoassays: Biological tools for high throughput screening and characterisation of combinatorial libraries, *Comb Chem High Throughput Screen* 2008, 11, 325-335.

Thornycroft, L. H.; Barnaby, S. W., Torpedo-Boat Destroyers, *Min. Proc. Inst. Chem. Eng*, 1895, 122 51-69.

G. Bauer, F. Pittner and Th. Schalkhammer, Metal Nano-Cluster Biosensors, Mikrochim Acta 131, 107-114 (1999).

Th. Schalkhammer, Metal Nano Clusters as Transducers for Bioaffinity Interactions, Monatschefte für Chemie 129, 1067-1092 (1998).

Y. Zhang et al., Metal-enhanced fluorescence form copper substrates, Applied Physics Letters, Apr. 25, 2007, vol. 90, pp. 173116_1-173116_3.

\* cited by examiner

PLASMONIC ELECTRICITY

CROSS-REFERENCE TO RELATED APPLICATIONS

This application is filed under the provisions of 35 U.S.C. §371 and claims the priority of International Patent Application No. PCT/US2009/057282 filed on Sep. 17, 2009, which in turn claims priority of U.S. Provisional Application No. 61/097,782 filed on Sep. 17, 2008, the contents of which are hereby incorporated by reference herein for all purposes.

BACKGROUND OF THE INVENTION

1. Technical Field

The present invention is directed to system that generates a current of electrical energy and additionally a detection system and method that detects fluorescence, luminescence, chemiluminescence or phosphorescence signatures in the form of an electrical signal conducted in metallic structures.

2. Background of Related Art

The identification and quantification of proteins and other biomolecules using bioassays are of great importance in biomedical and biochemical applications.[1-3] Fluorescence is the dominant technology in most of these applications, where a biomolecule of interest is detected by fluorescence emission from its fluorophore labeled binding partner.[4, 5] Fluorescence-based bioassays those carried out on planar surfaces generally lack sensitivity and require expensive optical instruments.[6, 7] In addition, the biorecognition events in these assays are inherently slow (several minutes to hours).[6, 7] The sensitivity of the fluorescence-based assays can be improved, without the use of high-end optical instruments, by incorporating plasmon resonant particles (PSPs) into these assays.[8, 9] The improved sensitivity is made possible by the increase in fluorescence signatures and decreased lifetimes of fluorophores placed in close proximity to PSPs, described by a phenomenon called Metal-Enhanced Fluorescence (MEF).[8, 10] In MEF-based bioassays, PSPs (generally silver nanoparticles) are deposited onto the planar surface and the bioassay is constructed on the PSPs.[8] Since the size of most biomolecules are smaller than PSPs (20-100 nm), fluorophores are positioned within a distance where their emission is increased due to their interactions with the surface plasmons of PSPs.[10]

The interactions of luminescent species with the close-proximity metallic nanoparticles have been extensively studied. These near-field interactions, are for the most part very complex, but can simply be understood phenomenologically as due to a close-proximity fluorophore inducing a mirror dipole in the metal, which in turn radiates the coupled quanta, in the form of emission, FIG. 1A. This interaction has been appropriately previously called "Metal-Enhanced Fluorescence".

For decades fluorescence-based technologies have relied on photo detectors to convert photon fluxes into digital signatures such as photomultiplier tube or charge coupled device (CCD) camera. Nearly all fluorescence based instruments encompass on or more of these types of detectors. However, such detectors are expensive and require an additional piece of equipment. Thus it would be advantageous to detect fluorescence without the need for such expensive detectors.

SUMMARY OF THE INVENTION

The present invention relates to detection systems and methods that detect fluorescence, luminescence, chemiluminescence or phosphorescence signatures in the form of an electrical signal conducted and emitted from metallic containing surfaces. Thus, the present invention provides for detecting fluorescence digitally and directly without the need for expensive detectors.

In one aspect the present invention relates to a system for generating electrical current, the system comprising:
  a substrate comprising metallic material positioned on the substrate, wherein the metallic material is shaped as particles, nanostructures, island or colloids and at least partially covered with a polar solution;
  a set of electrically conductive electrodes communicatively contacting at least two of the metallic particles positioned thereon;
  an intrinsic or extrinsic fluorophore positioned near the metallic material, wherein excitation of the fluorophore by electromagnetic energy induces a mirror dipole in the metallic material causing plasmonic current flow for storage or directing to a current reading device.

Importantly the current is increased as the amount of binding fluorophores increases, thereby providing for an assay that provides an electrical signal proportional to the amount of binding fluorophores.

In another aspect the present invention relates to an assay detection method comprising:
  providing a conductive metallic material on a substrate; wherein the metallic material is shaped as a non-continuous film, particles, nanostructures, island or colloids and wherein the substrate has a first end and an opposing second end;
  communicatively contacting the first and second end of the substrate and at least two of the metallic particles positioned thereon to a first and second electrode, wherein the first and second electrodes are communicatively connected to a current reading device;
  introducing at least one biomolecule for disposing near the conductive metallic material, wherein the biomolecule is capable of inducing a mirror dipole in the metallic material and such dipole is enhanced by a predetermined proximity to the metallic material;
  applying electromagnetic energy from an electromagnetic energy source to excite the biomolecule and inducing a mirror dipole in the metallic material causing plasmonic current flow; and
  measuring the plasmonic current flow by the current flow detector.

The method and system described above may be used in multiple detecting systems, including but not limited to, immunoassays, hybridization assays, resonance energy transfer assays, polarization/anisotropy based assays, chemiluminescence based assays, luminescence based assays, enzyme-linked immunosorbent assays.

In another aspect, the present invention provides for a detection system comprising:
  a conductive metallic material positioned within a container, wherein the metallic material is shaped as a non-continuous film, particles, nanostructures, island or colloids, a conductive metallic material on a substrate;
  at least one fluorophore for disposing near the conductive metallic material, wherein the fluorophore is capable of inducing a mirror dipole in the metallic material and such dipole is enhanced by a predetermined proximity to the metallic material;
  a first and second electrode communicatively connected to at least two of the metallic particles positioned thereon, wherein the first and second electrodes are communicatively connected to a current reading device;

an electromagnetic energy source to excite the fluorophore and to induce a mirror dipole in the metallic material causing plasmonic current flow, wherein electromagnetic energy source is positioned a distance from the first or second electrode to increase current to be detected by the current reading device.

In the present embodiment, the biomolecule comprises a fluorescing component that has the ability to fluoresce when contacted with radiation in the range from UV to IR.

In another aspect the present invention relates to a method of metal-enhanced fluorescence sensing, comprising:

applying a conductive metallic material to a surface used in a detection system, wherein the surface includes glass, quartz, or a polymeric material, wherein the surface has a first and second end, wherein the first and second end and at least some of the metallic material is communicatively connected to a first and second electrodes with a current measuring device positioned therebetween;

introducing a polar solution containing at least one biomolecule for disposing near the conductive metallic surface, wherein the biomolecule is capable of excitation causing either a dipole moment or fluorescing;

exciting the biomolecule with an electromagnetic source to cause the dipole moment or fluorescing and whereby such excitement induces a dipole in the metallic material causing plasmonic current flow;

measuring the plasmonic current flow with the current reading device, such as ampmeter.

Preferably, the electrodes are separated by a sufficient distance to provide optimal current readings, wherein the separation is from about from about 5 nm to 100 nm.

In yet another aspect, the present invention provides a method for detecting a targeted pathogen in a sample without the use of a photodetector, the method comprising:

providing a system comprising:

an immobilized metallic material positioned on a surface substrate in a polar solution, wherein the substrate has a first and second end and wherein the first and second end of the substrate include electrodes or at least some metallic material are communicatively connected to a first and second electrode, wherein the immobilized metallic material has attached thereto an immobilized capture DNA sequence probe complementary to a known DNA sequence of the target pathogen; and a free capture DNA sequence probe complementary to a known DNA sequence of the target pathogen, wherein the free capture DNA sequence probe has attached thereto a fluorophore;

contacting the sample with the immobilized capture DNA sequence probe, wherein any DNA sequence of the target pathogen binds to the immobilized capture DNA sequence probe;

contacting the bound DNA sequence of the target pathogen with the free capture DNA sequence probe, wherein binding of the free capture DNA sequence probe to the DNA sequence of the target pathogen causes the fluorophore to be positioned a sufficient distance from the immobilized metallic material to induce a dipole in the metallic material;

irradiating the system with electromagnetic energy in a range from UV to IR to excite the fluorophore positioned a predetermined distance from the metallic material; and measuring the plasmonic current flow with a current flow detector positioned between the electrodes, wherein the current is proportional to the amount of fluorophores.

Preferably, the conductive metallic material takes the form of metallic particles, such as, nanostructures, islands, colloids, porous matrix or a semi-continuous metallic surface. The metallic element may include any form of metals such as silver, gold, platinum, zinc, aluminum, indium, palladium, rhodium iron, nickel and copper, and more preferably the metallic material is silver, such as a low-density silver. The substrate can include, glass, quartz and/or a polymeric material.

Preferably, the metallic material is in the form of particles and separated a distance to provide optimal current flow and wherein resistance is higher than that of a continuous metal film. Preferably, at least a portion of each metallic particle is in contact with a polar solvent or a dipolar aprotic solvent that has a dipole moment and inducible, such as water, other polar solvents, including methanol or acetic acid, ionic salt solutions and/or acetone, ethylene acetate.

The molecule that is capable of fluorescing and/or upon excitation by electromagnetic energy exhibits a dipole moment includes, but is not limited to fluorophores, chromophores, lumophores or biomolecules that include extrinsic luminescence activity.

In one aspect, the present invention relates to bioassay systems comprising metallic surfaces for the enhancement of effects of chemiluminescence based reactions positioned near the metallic surfaces, wherein metallic surface plasmons are excited by a chemically induced electronically excited state of a chemiluminescent species and transference of energy from the chemiluminescence reaction induces plasmonic current flow in the metallic structures that can be measured with a current flow device.

In a still further aspect, the present invention relates to an assay, the method comprising:

providing at least one vessel or container; wherein a first and second electrode are positioned within the vessel or communicatively connected thereto;

introducing metallic nanostructures into the vessel, wherein the vessel includes a polar solution, wherein the metallic nanostructures can be free in solution or connected to a surface of the vessel and communicatively connected to the first and second electrodes;

introducing a molecule that exhibits dipole activity upon excitation and disposing such molecule near the metallic nanostructures, wherein the metallic nanostructure is positioned a predetermined proximity to the metallic nanostructures to induce a mirror dipole in the metallic nanostructures; and measuring the current flow.

In yet another aspect, the present invention relates to a method of metal-enhanced chemiluminescence sensing, comprising:

applying a metallic material to a surface used in a detection system, wherein the surface or metallic material is connected to a set of electrodes; introducing a solution containing at least one biomolecule for disposing near the metallic surface, wherein the biomolecule comprises a chemiluminescent label;

triggering the chemiluminescent label to induce a chemically electronically excited state thereby generating metallic surface plasmons and inducing a mirror dipole in the metallic material and generating a current flow in the solution.

In another aspect, the present invention relates to a system for measuring chemiluminescence, the system comprising:

a partially metalized surface positioned on a surface substrate, wherein the metalized surface is in contact with a polar solvent wherein the substrate or partially metallized is connected to a set of electrodes;

a connector molecule attached to the partially metallized surface or near the partially metallized surface for binding or capture of a desired molecule in a testing sample;

a detector molecule having an affinity for the desired molecule, wherein the detector molecule comprises a chemiluminescence label;

a triggering component that chemically reacts with the chemiluminescence label to generate a chemically induced electronically exited state and induce a mirror dipole in the partially metallic surface and inducing a current flow in the polar solvent, wherein the current flow is measured and such flow is proportional to the amount of desired molecule in the testing sample.

A system for conducting current, the system comprising:
1. metallic particles dispersed in a polar solution, wherein the metallic particles are adaptable for connecting to an intrinsic or extrinsic fluorophore molecule; and
2. a source of electromagnetic energy to deliver radiation in a range of UV to IR and in an amount sufficient to excite the fluorophore, wherein such excitation causes a mirror dipole in the metallic particles and induces current flow in the solution.

Still further, the present invention relates to using the present concept of plasmonic electricity in combination with a microscope that can provide visual images and a direct digital readout of induced plasmonic current flow, wherein the system includes a substrate having metallic particle deposited thereon, wherein the substrate is a slide adapted for use in a microscope and the substrate or two of the metallic particles are adapted with electrodes and attached to a current reading device.

Other aspects and advantages of the invention will be more fully apparent from the ensuing disclosure and appended claims.

DETAILED DESCRIPTION OF THE INVENTION

The present invention relates to systems and methods for generating a current flow by positioning a fluorophore near a metallic particle and wherein excitation of the fluorophore causes an induced mirror dipole in the metallic particle and a flow of electrical current from one metallic particle to an adjacent metallic particle in communicative contact in a polar solvent.

Figure 1A:
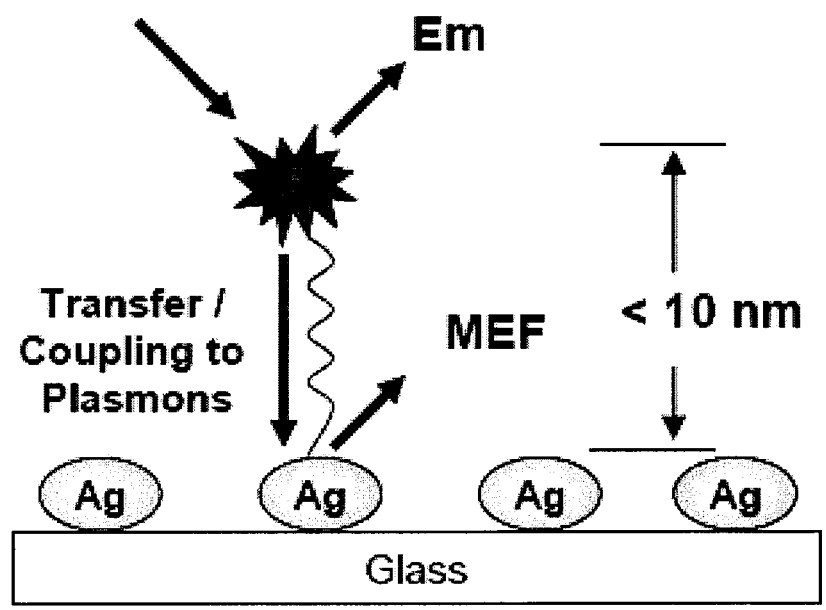
FIG. 1 shows graphical representation of the current interpretation of Metal-Enhanced Fluorescence (A), Plasmonic Current is due to coupling of excited fluorophore to the surface plasmons of silver nanoparticles (B), a electrode setup with attached ammeter for measuring current, F—Fluorophore, MEF—Metal-Enhanced Fluorescence, PC—Plasmonic Current, Ag—Silver nanoparticles.
Figure 1B:
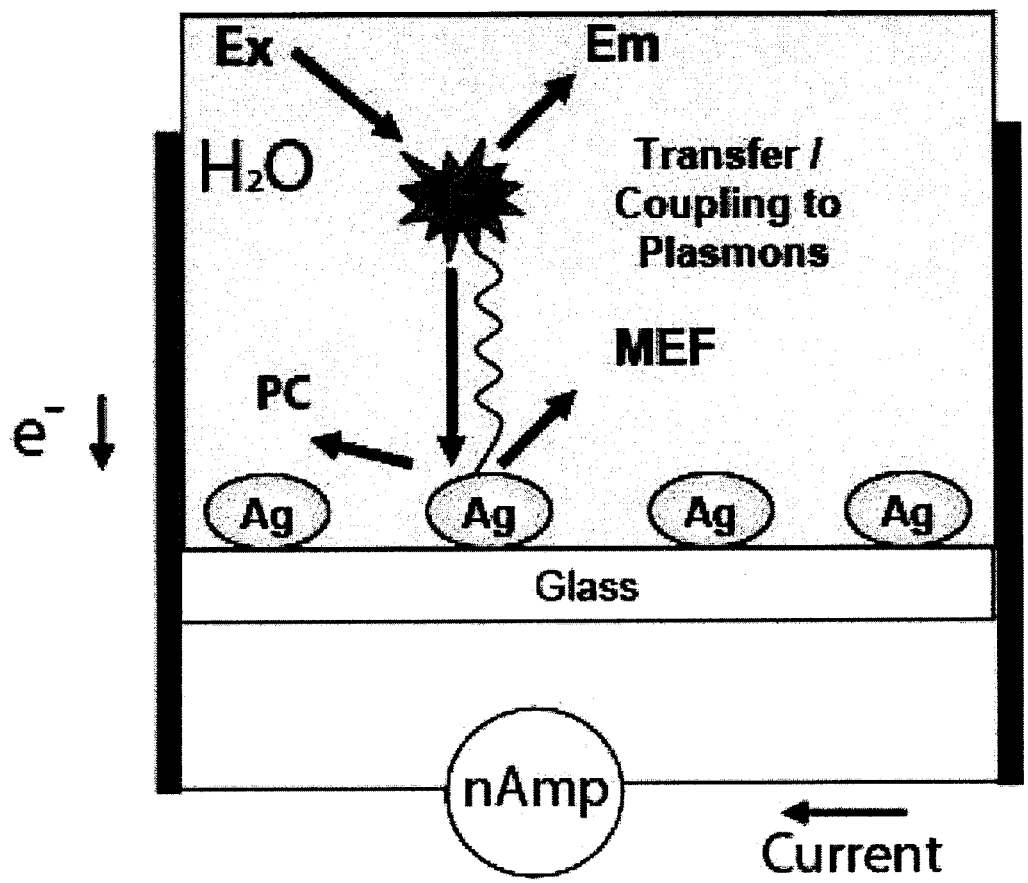

The present invention describes the detection of fluorescence (luminescence, chemiluminescence, phosphorescence) signatures in the form of electrical signals in thin metallic films. Normally, fluorescence or luminescence emission is detected with a detector, PMT (Photomultiplier tube) or CCD (charge coupled device) camera etc. However, fluorophores in close proximity to the metal can induce currents in the metal, which can be detected using an ammeter as shown in FIG. 1B.

Figure 2:
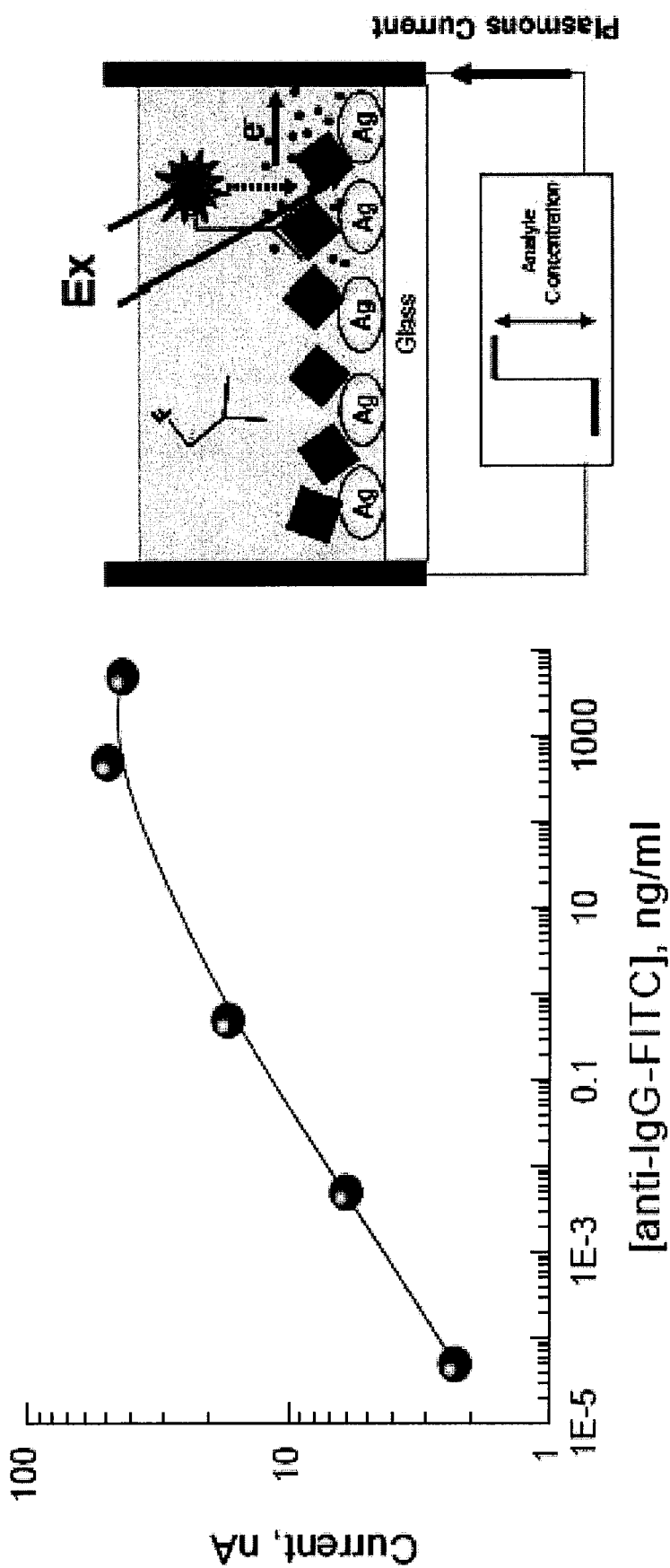
FIG. 2 shows dependence of the plasmonic current (PC) in the SiF covered by rabbit IgG upon the concentration of added anti-IgG, labeled with fluorescein with graphical interpretation of the experiment.

The notion of direct detection of fluorescence is an enormous breakthrough in fluorescence spectroscopy and its applications. Potential uses for this technology include immunoassays, textiles and fabrics that provide metallic containing structures that can be used to powers hand held devices wherein the antigen concentration can now be read directly and most importantly digitally, as shown in FIG. 2, without the need for an external detector. Another application is in solar energy conversion, where daylight excited fluorophores can generate electrical currents in thin metallic films.

"Fluorophore," as used herein, means any substance that can be excited by electromagnetic energy and induce a mirror dipole metallic surface in close proximity to the metallic surface and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2[(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4,6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, green fluorescent proteins and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Also included are novel quaternary nitrogen heterocyclic boronic acid-containing compounds including:

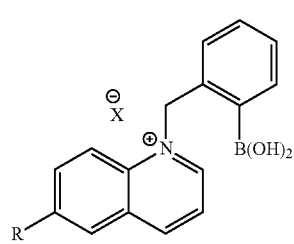
(A)

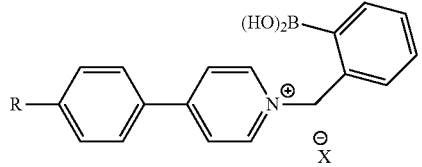
(B)

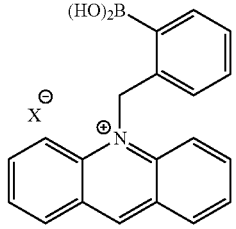
(C)

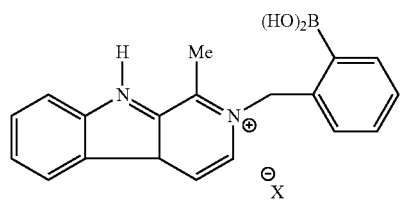
(D)

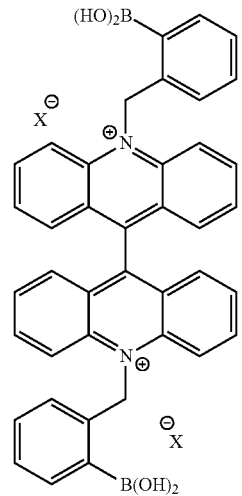
(E)

and

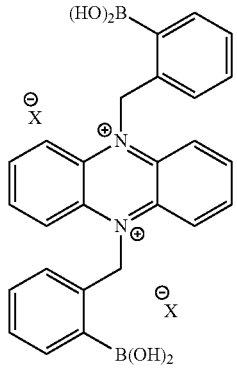
(F)

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups.

Embodiments of the present invention are applicable to chemiluminescence labels or moieties which participate in light-producing reactions in the presence of a triggering agent or cofactor. In the present application, for purposes of example and without limitation, a preferred embodiment will be discussed in terms of chemiluminescence labels and triggering agent. The label affixed to the detector molecule will be referred to as the "label" or "label agent". For purposes herein, "triggering agent or cofactor" is broadly used to describe any chemical species, other than the chemiluminescence labels which participate in a reaction and which produces a detectable response. Chemiluminescence labels and triggering agents produce a light response.

Examples of suitable chemiluminescence labels include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen.

Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio)proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

Techniques for attaching antibodies or antigens to solid substrates are also well known in the art. For example, antibodies may be coupled covalently using glutaraldehyde to a silane derivative of borosilicate glass.

The term "biomolecule" means any molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Preferably, the biomolecule has a dipole moment when excited and thus can induce a mirror dipole in a metallic material in close proximity. Exemplary biomolecules include nucleic acids, aromatic carbon ring structures, NADH, FAD, amino acids, carbohydrates, steroids, flavins, proteins, DNA, RNA, oligonucleotides, peptide, nucleic acids, fatty acids, myoglobin, sugar groups such as glucose etc., vitamins, cofactors, purines, pyrimidines, formycin, lipids, phytochrome, phytofluor, peptides, lipids, antibodies, bilirubin, tryptaphan and phycobiliproptein.

There are many important assays that can directly benefit from immediate readouts and quicker kinetics. For example, myoglobin concentrations for heart attack patients, patients of toxic shock and pancreatitis. Thus, the present invention may optionally include the use of microwave energy or sonic energy to increase any reaction rates in an assay detection system. As such, the present invention can be used for points-of-care clinical assessment in emergency rooms.

The present invention may optionally include the use of microwave energy or sonic energy to increase any reaction rates in an assay detection system The assay systems of the present invention may further comprise a light or laser source for directing an energy beam on any included fluorophore to provide excitation energy. The laser beam may be positioned adjacent to the system for directing the beam at the molecular components. The laser may be any device capable of focusing an energy beam at a particular point on the solid or liquid source material for excitation and the laser may transmit RF, infrared, microwave to UV energy.

Any source, known to one skilled in the art may be used, such as a laser that emits light, wherein light is used in its broad sense, meaning electromagnetic radiation which propagates through space and includes not only visible light, but also infrared and ultraviolet radiation. Thus, a single instrument placed above the surface of the assay can be used to generate the energy to excite fluorescing molecules. The light can be emitted from a fiber continuously or intermittently, as desired.

Further, 2-photon excitation may be used at approximately 375 to 900 nm using continuous or short pulse width (<50 ps), high repetition rate (>1 MHz), laser diode sources. A variety of pulsed laser diode sources that will be compatible with fluorophores can be used with the present invention and are commercially available.

Still further, the present invention can be used with tunable Ti:Sapphire laser excitation and multiphoton microscopy.

The present invention provides for metallized islands of elliptical, spherical, triangular or rod-like forms. In exemplary cases, the elliptical islands have aspect ratios of 3/2, and the spherical colloids have diameters of 20-60 nm. However, the invention is not limited to any particular geometry. Using known coating techniques, the placement of metallic islands could be controlled precisely, as close as 10 to 50 nm apart.

The metallic material may be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which species will flow and be both detected and counted more efficiently.

The emission induction of a mirror dipole from the excited fluorophore to the metallic may be observed at distances according to the type of fluorophore to be detected and the type of metal. For example, induction of a current may be observed when a fluorophore distances about 5 nm to about 200 nm to metal surfaces. Preferable distances are about 5 nm to about 50 nm, and more preferably, 10 nm to about 30 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Different surface enhanced fluorescence effects are expected for mirrors, sub-wavelength or semi-transparent metal surfaces, silver island films or metal colloids. More dramatic effects are typically observed for islands and colloids as compared to continuous metallic surfaces. The silver islands had the remarkable effect of increasing the intensity 5-fold while decreasing the lifetime 100-fold. Such an effect can only be explained by an increase in the radiative decay rate.

Preparation of Metal Islands

The island particles are prepared in clean beakers by reduction of metal ions using various reducing agents. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Alternative procedures for preparing metal particles are also available. Silver is primarily used because of the familiar color from the longer surface plasmon absorption of silver.

Preparation of Silver Colloids

Colloids can be prepared as suspensions by citrate reduction metals. Preferred metals are silver and gold. Again, gold may be because of the absorption of gold at shorter wavelengths. However, gold colloids may be used with longer wavelength red and NIR fluorophores.

The size of the colloids and their homogeneity can be determined by the extensive publications on the optical properties of metal particles available and the effects of interface chemistry on the optical property of colloids.

Silver island films can be formed by a chemical reduction of a silver salt on the quartz surface, which are relatively simple to fabricate. However, this approach does not provide a control of particle size, or distance of the fluorophores from the surface. Enhancements of 1000 fold have been with the realization that sample geometries have been heterogeneous and the enhancement factors spatially averaged.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.[90, 91, 92]

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

The electrode system of the present invention may include a containment vessel that includes two electrodes, anode and cathode, attached to the vessel or the electrode can be inserted into solution. Generally the electrodes can be fabricated from any conductive metal and may include carbons, noble metals or alloys of Pt, Pd, Ir, Au, Ru, etc., noble metals or alloys deposited on a substrate such as Ti or Ta. Metals and metal alloys are preferred having a conductivity of greater than about $10^{-4}$ S/cm. In the alternative, wire electrodes can be directly attached to two of the metallic particles, wherein the metallic particles and attached wires are separated sufficiently to detect optimal current flow.

Further, the electrodes can be fabricated from any electrically conducting polymer, electrically conducting ceramic, electrically conducting glass, or combinations thereof including metal oxides and selected from tin, lead, vanadium, titanium, ruthenium, tantalum, rhodium, osmium, iridium, iron, cobalt, nickel, copper, molybdenum, niobium, chromium, manganese, lanthanum, or lanthanum series metals or alloys or combinations thereof, and possibly containing additives like calcium to increase electrical conductivity.

Electrolyte or polar solvents may include an ionically conductive aqueous or non-aqueous solution or material, which enhances the movement of current between electrodes.

This embodiment of the present invention may also have vast applications in clinical medicine, environmental monitoring applications, homeland security such as rapid detection of low concentration species with a direct and digital readout, industrial processes, pharmaceutical industries such as monitoring species, and sensors for use in reduced atmospheres such as biohazard clean rooms and space light.

Figure 3A:
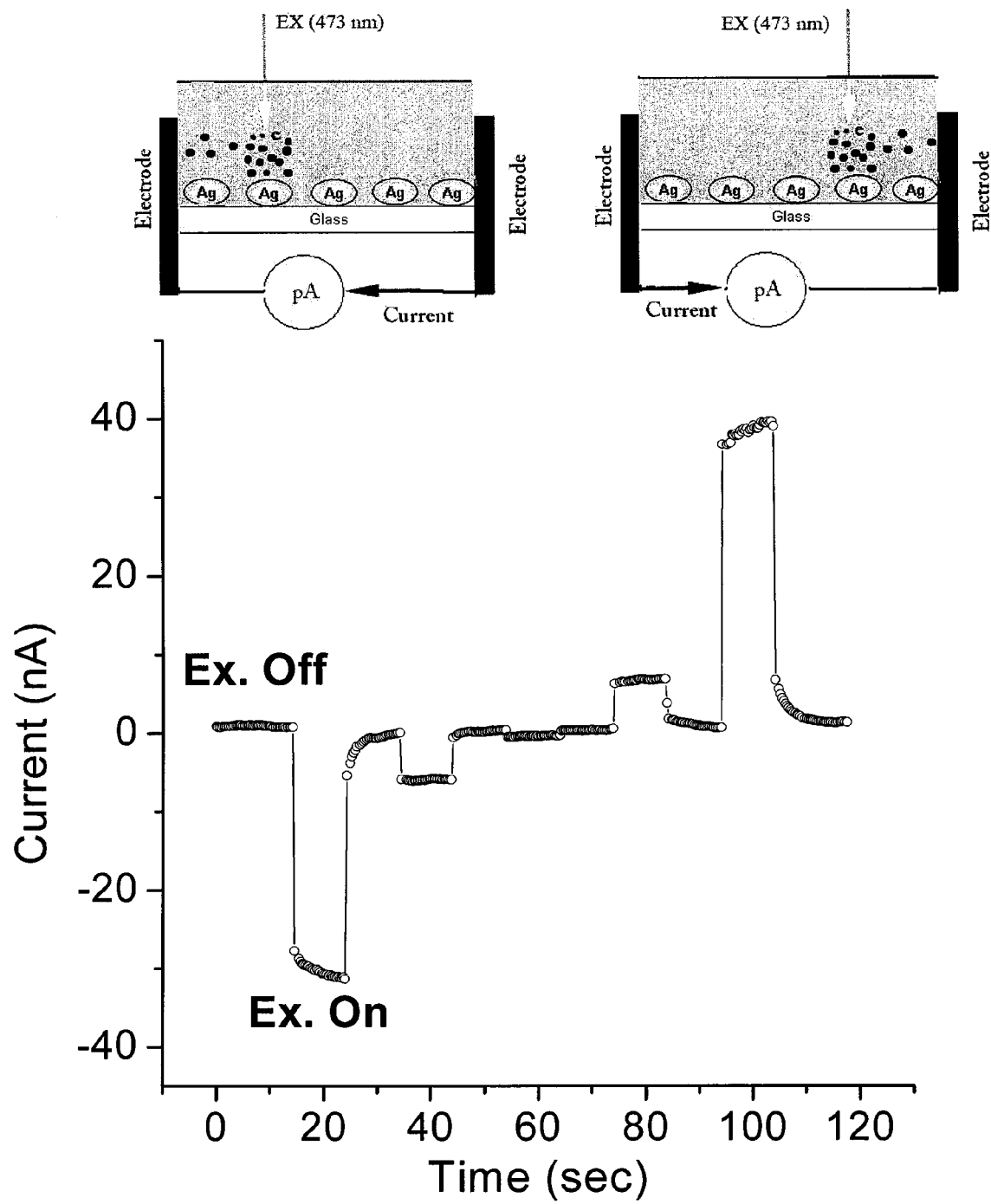
FIG. 3A shows plasmonic current (PC) induced by the laser (473 nm) in SiF (R>>200 MOhm/cm) covered by FITC in water. The distance between electrodes is 10 mm. The excitation spot on SiF was moved from the left electrode to the right electrode.
Figure 3B:
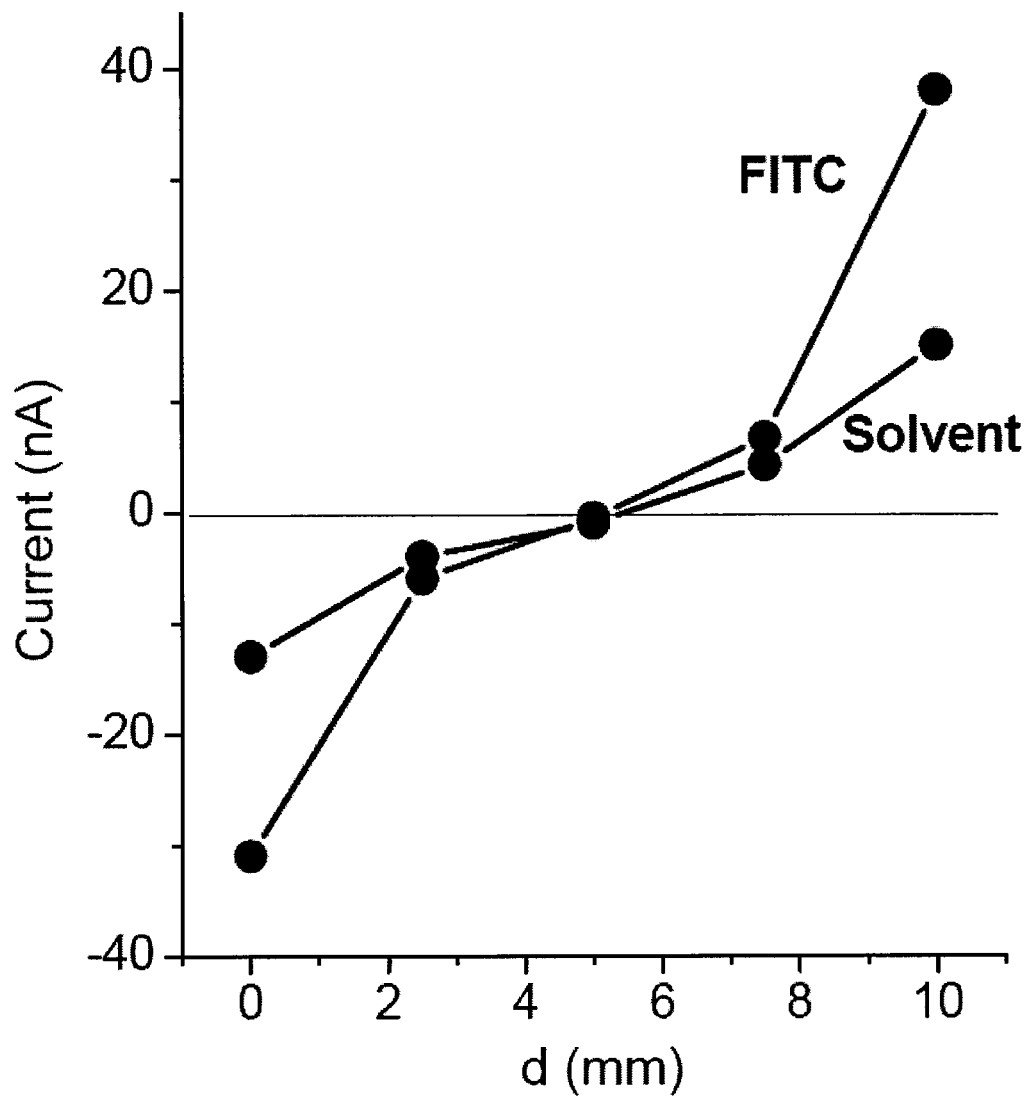
As shown in FIG. 3B, the direction of observed plasmonic current flow, non-linearly depends on the distance of the excitation spot from the electrodes themselves.

When a fluorophore induces a mirror dipole in the metal, near-field photo-induced currents (photo currents) are formed. These very small currents are able to migrate across silvered films. Interestingly, the greater the concentration of fluorophore present, there is a corresponding increase in induced current. FIG. 3, shows the extent of photo-induced current on the concentration of fluorescein (a fluorescent probe) in water, placed between 2 electrodes on a silver island film. Remarkably, the current increases significantly over the 3 $\log_{10}$ concentrations of fluorescent probe studied. This result suggests that the more fluorophore present close to metal, then the greater the induced current flow. It is interesting to note, that in Traditional Fluorescence-based immunoassays, the extent of detected fluorophore (usually fluorescence intensity) is directly related to the analyte concentration to be determined in the assay. The results shown herein suggest, that fluorescence-based immunoassays can be constructed on silvered surfaces, where the concentration of analyte (antigen) can be determined by the induced currents in the metal, as depicted by FIG. 1A and FIG. 2. Remarkably, the reading is purely digital and is a direct measure of the coupled fluorescence. In contrast, fluorescence based immunoassays in the world today, detect the fluorescence from the assay directly, then covert the signal which can be displayed digitally. Subsequently, the present approach is a significant breakthrough in how fluorescence is measured and quantified. FIG. 3A also demonstrates that the direction of current flow can be determined by the position of the excitation spot relative to the sampling electrode. The current is directly symmetrical, i.e. a positive or negative current, with regard to the position of the laser spot and the electrode.

Figure 4:
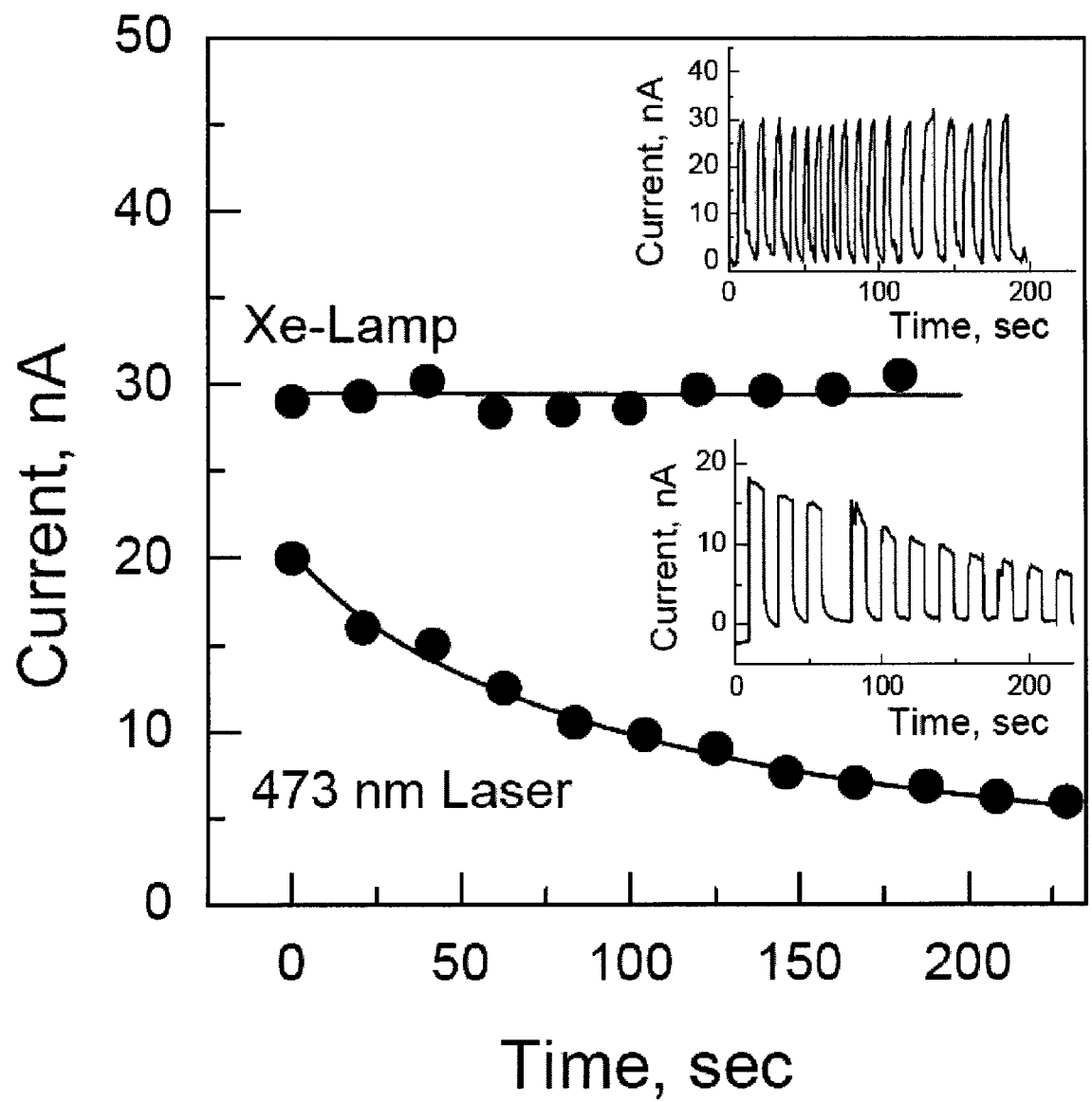
FIG. 4 shows irradiation of FITC-SiFs (H2O) using a Xe-arc lamp and also a 473 nm laser.

Other Potential Uses of the Technology:

While direct measurement of fluorescence-based signatures is a big field (business) in itself, one very promising application of the technology is likely to be in solar energy conversion. It is also envisioned that fluorophore coated substrates can induce currents in metal films after sun light illumination, FIG. 4. In this figure, a Xenon arc lamp is used to simulate sun light. As can be seen in FIG. 4—top, insert, as the sun light is gated on and off, the current modulates, demonstrating that the effect is due to direct illumination of SiFs/fluorophores with light. Laser light also causes plasmonic current as shown in the bottom figure of FIG. 4.

Figure 5:
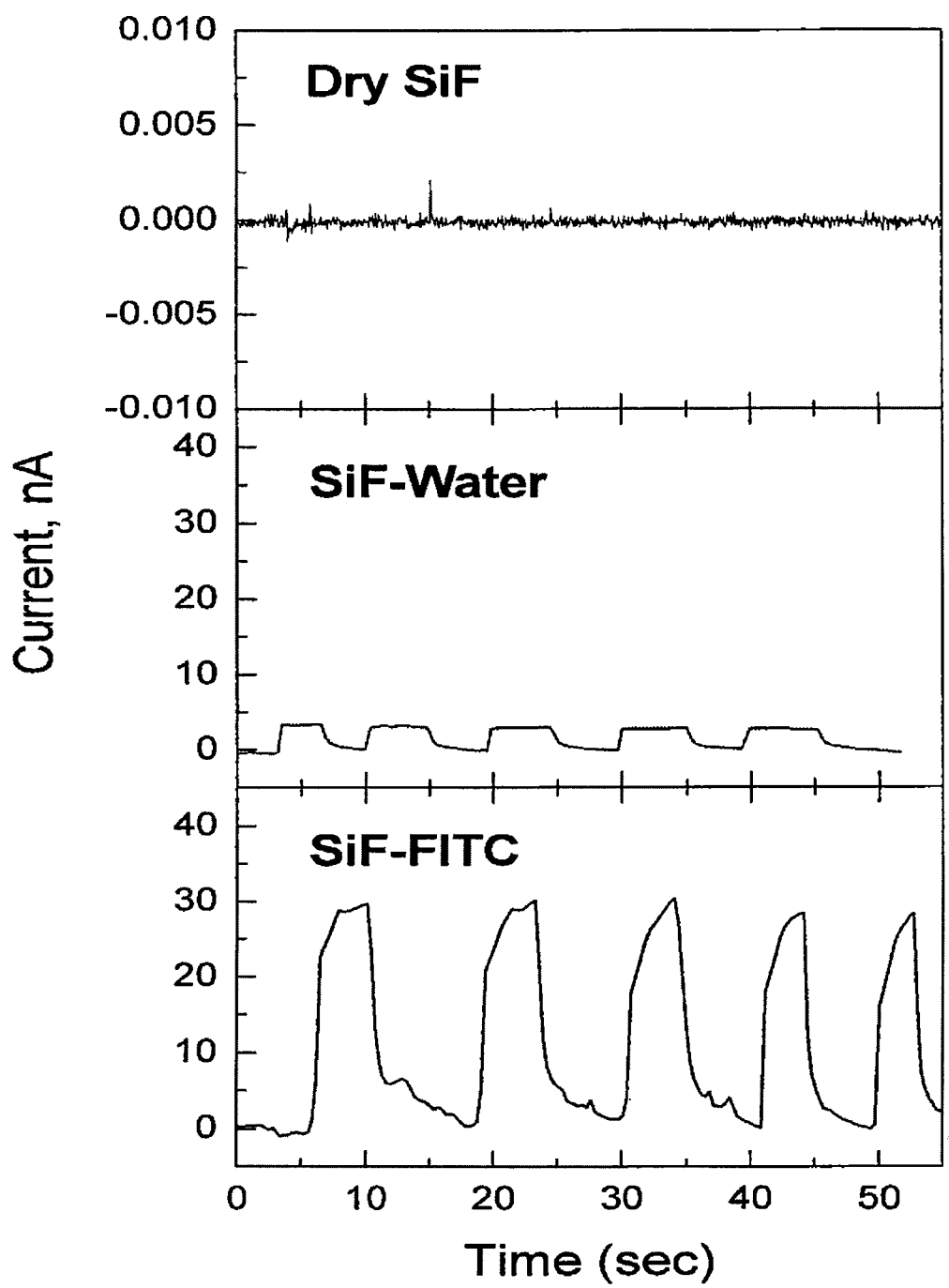
FIG. 5 shows Top: Current induced in SiFs (dry sample); Middle: Current induced by wet SiFs (H2O); Bottom: SiFs coated with (FITC)-water solution. Irradiation of the slides was performed with a Xe-arc lamp. Manual light shut off was achieved sharply in about 5 sec intervals. SiF—Silver Island Films.
Figure 6A:
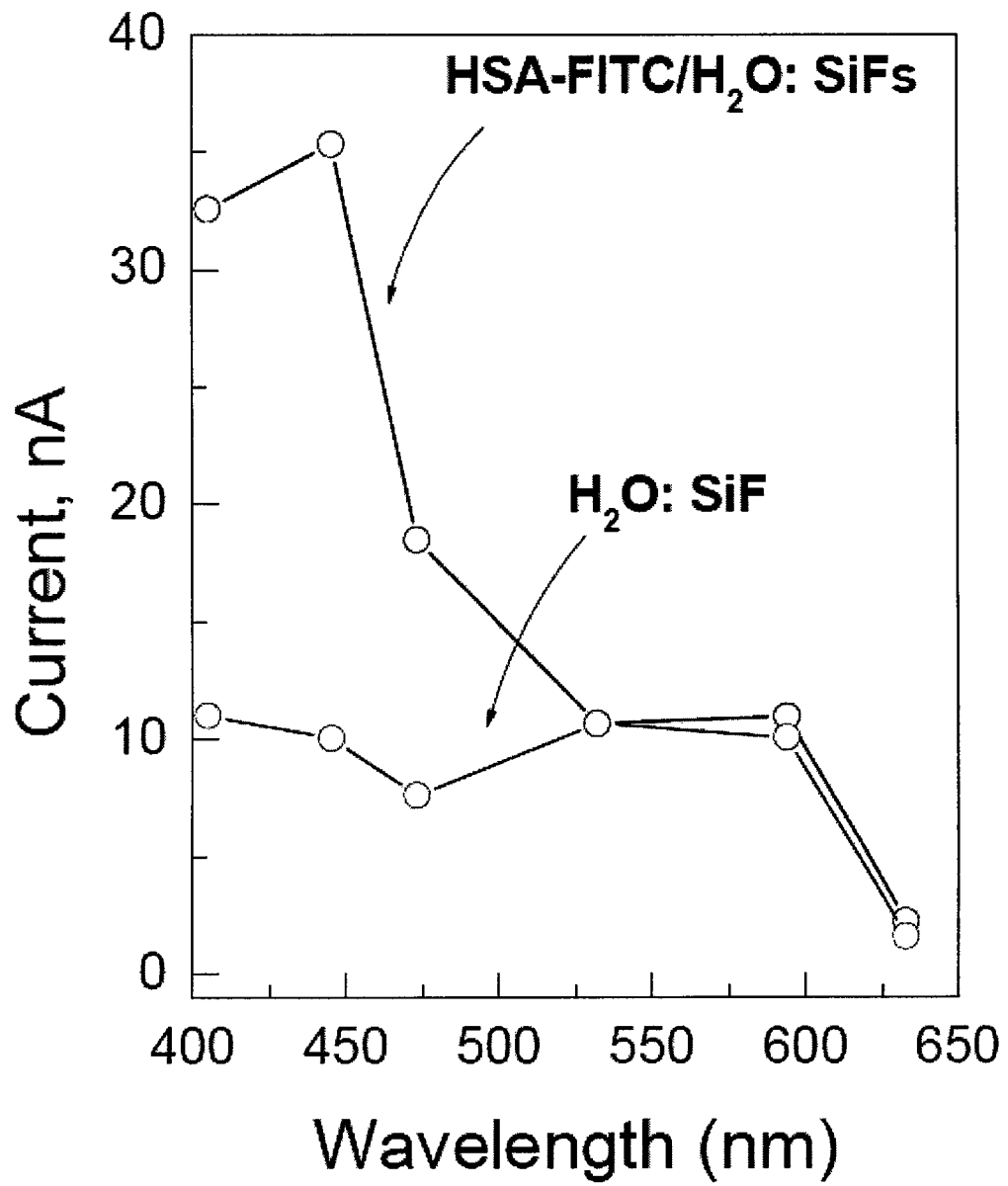
FIGS. 6A and B show the dependence of the current, induced by light in SiF containing deposited human serum albumin labeled by FITC (HSA-FITC) or solvent (water), upon wavelength of excitation. (a) observed current corrected on Laser power deviations; (b) Contribution of the HSA-FITC to the current, absorption of the SiF and FITC. Excitation was done by lasers. Power of light generation was adjusted by the neutral filters (NF) to about 20-50 mW. Correction of the current at certain wavelengths was done by normalizing to the power of 46.5 mW (power of 473 nm-Laser (500 mW) attenuated by N-filter (OD473=1.04 o.u.). [HSA-FITC]=0.65 mM in water, pH 5.5.
Figure 6B:
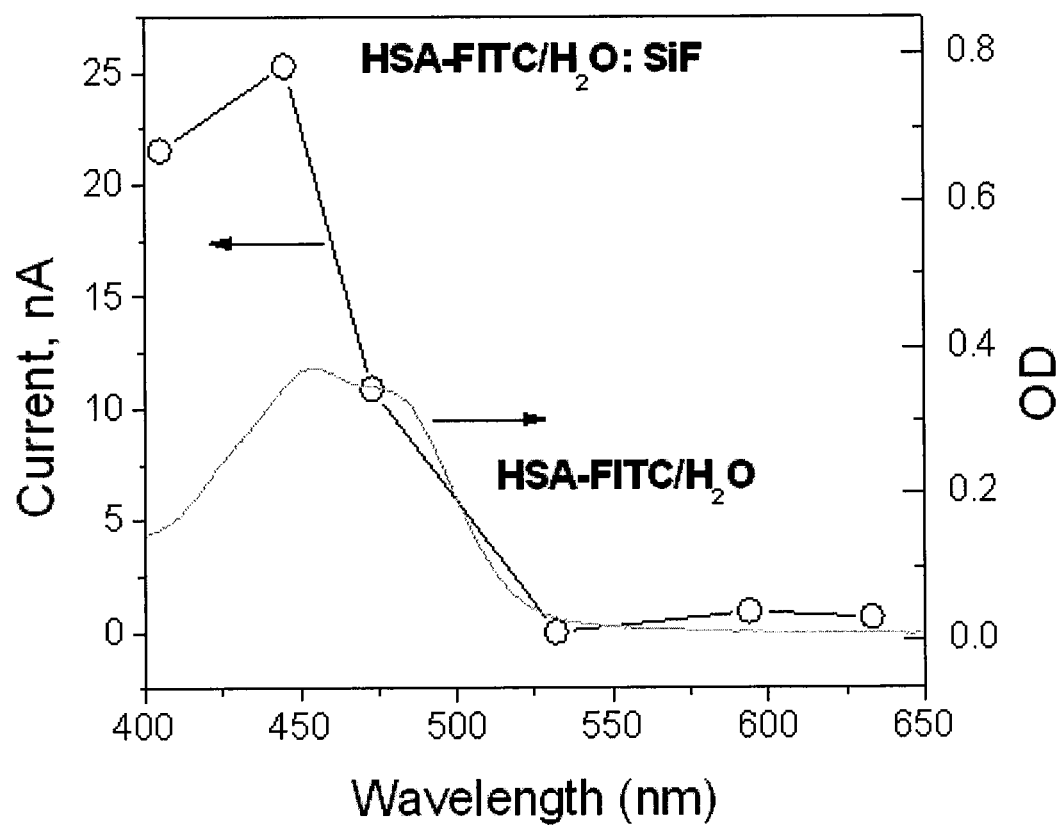
Figure 7:
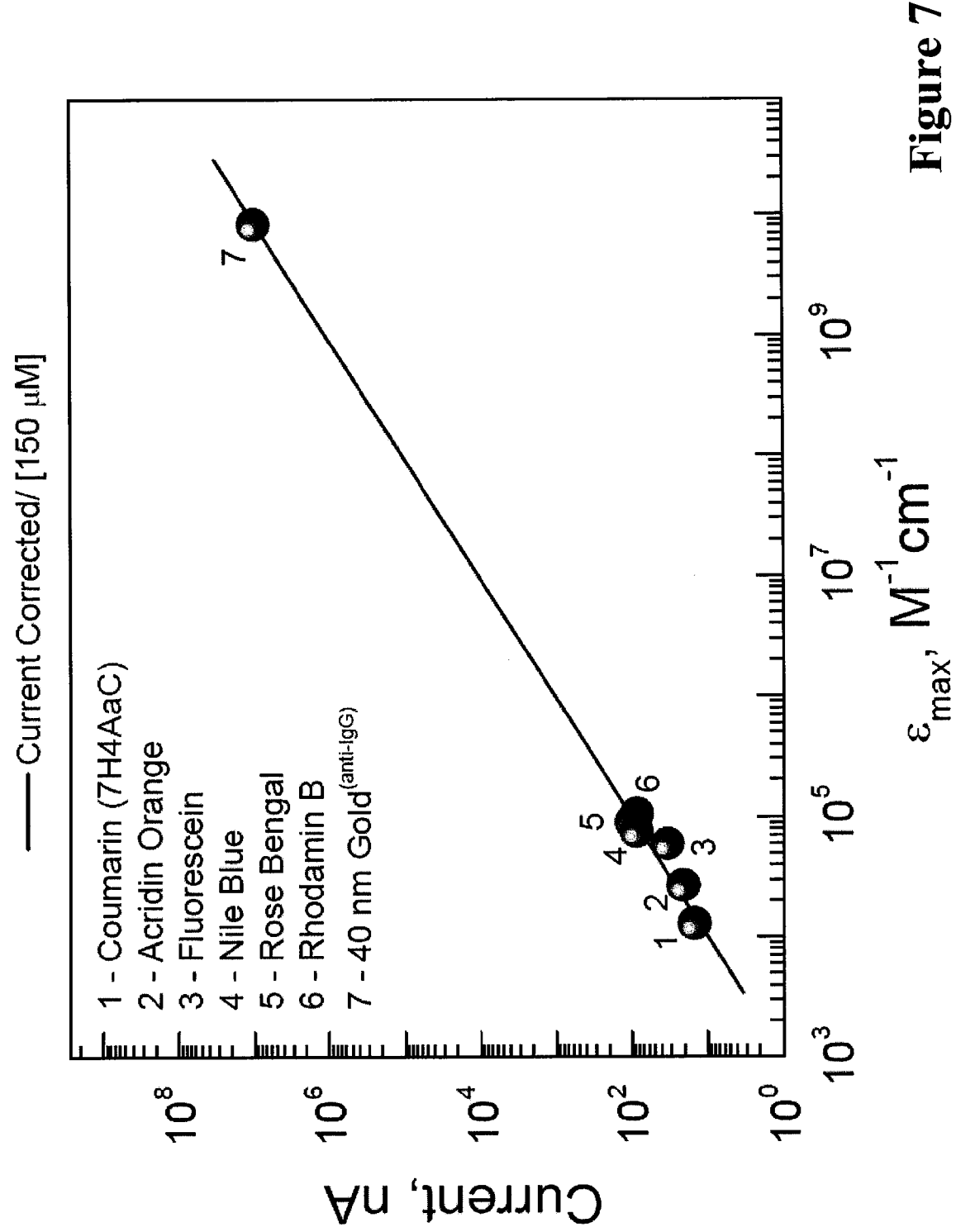
FIG. 7 shows the dependence of the current, generated by SiF-Dye system upon 473 nm laser irradiation, on extinction coefficient of the studied dyes. Observed current was normalized to the current induced by dyes at the Concentration of 150 mM, taking linear dependence of the current vs dye Concentration.

Demonstration of Plasmonic Current/Electricity:

FIG. 5—top shows that dry Sifs (Silver Island Films) have little to no current in them when illuminated by an external light source, a value of 0 nA determined. However, when an aqueous solution is placed on top of the SiFs a current of <5 nA is produced. Interestingly, the current modulates as the Xe-arc lamp light source is modulated on-off. This background current is due to the water dipole interaction with the metal SiFs. However, when a fluorophore (fluorescent, phosphorescent or chemiluminescent species) is added to the water solution on SiFs, a significant current is further observed, increasing to as much as 30 nA. This current is due to interaction of the fluorophore dipole with the metal, as graphically indicated in FIG. 1B. As can be seen from this figure, the presence of fluorophores close to Sifs (and indeed other metals) causes a current, which is directly proportional to the concentration of fluorophore, making it an excellent technology for the direct detection of Fluorescence. In addition and remarkably, the current generation in the metal is wavelength dependent and appears to follow both the absorption spectra of the Sifs and the emission spectra of the metal, as shown in FIGS. 6A and B. In addition, the magnitude of the induced current is dependent on the molar extinction coefficient of the close-proximity dipole, FIG. 7, which implies that other plasmonics nanostructures will be excellent for inducing a larger magnitude current, see below, FIGS. 8-11.

Figure 8:
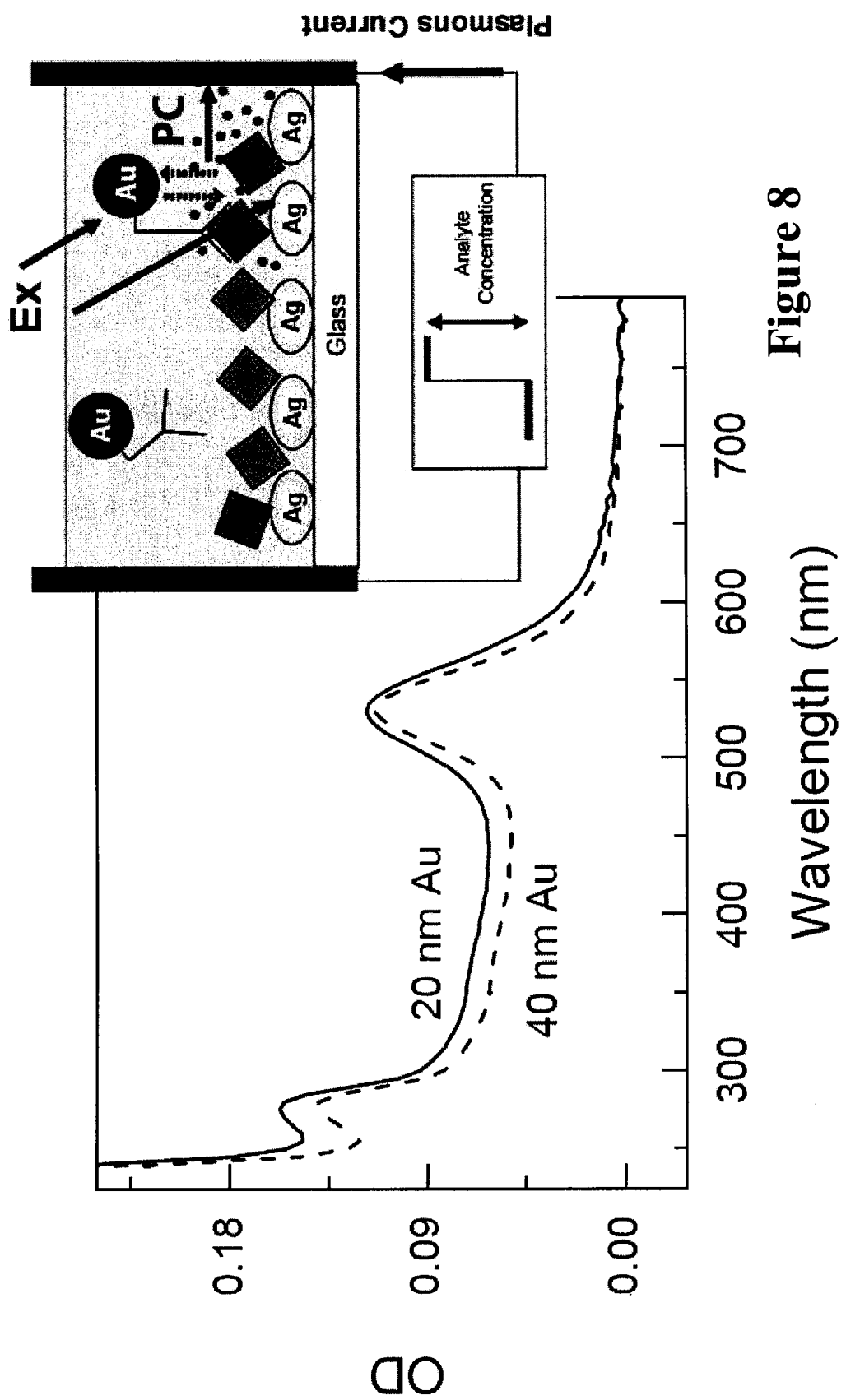
FIG. 8 shows the absorption spectra of 20 nm and 40 nm Gold conjugate anti-IgG (Rabbit). Insert: Graphical representation of the model immunological assay (IgG—anti-IgG) based on Plasmon Current (PC) upon light excitation. Ag—silver islands; Au—gold nanoparticle conjugated to anti-IgG.
Figure 9:
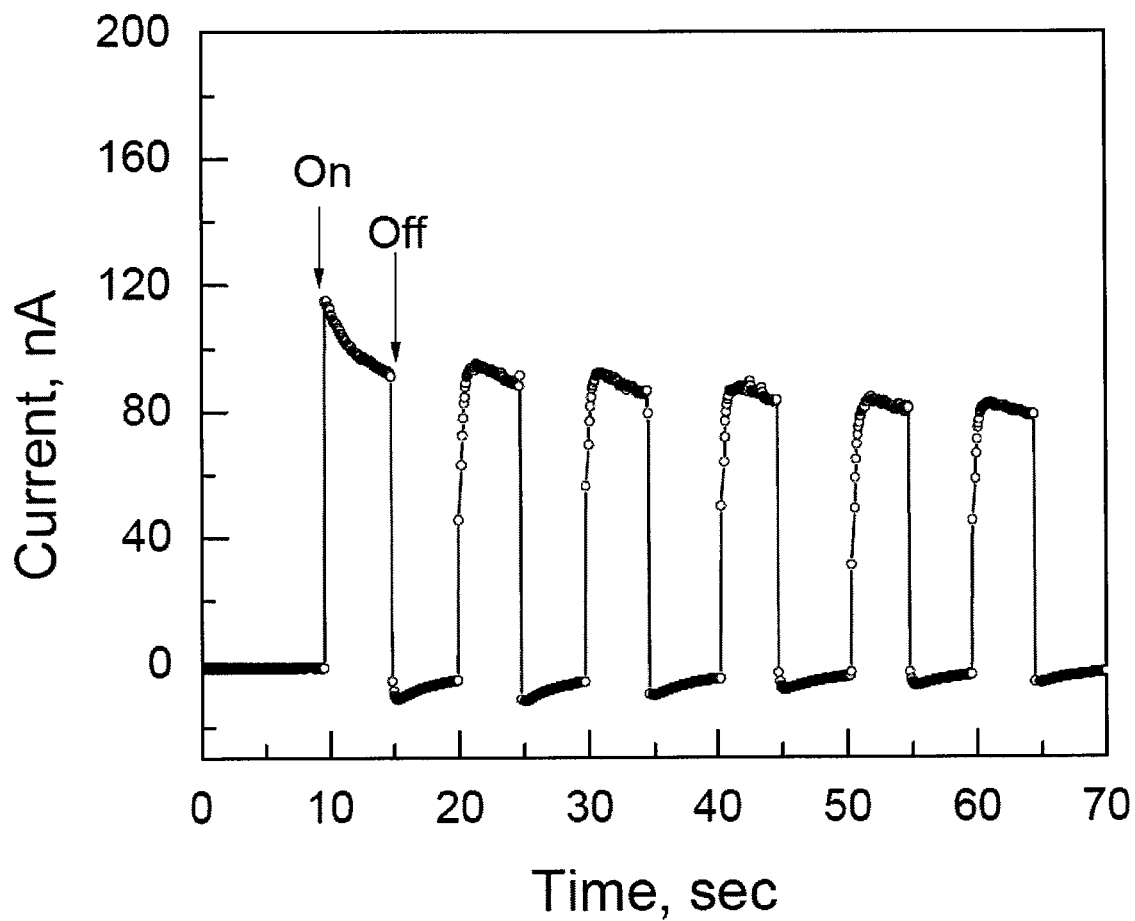
FIG. 9 shows current induced in SiF-IgG covered with 40 nm Gold conjugate anti-IgG. lex was 473 nm and the concentration of Gold—anti-IgG was 0.1 nM.
Figure 10:
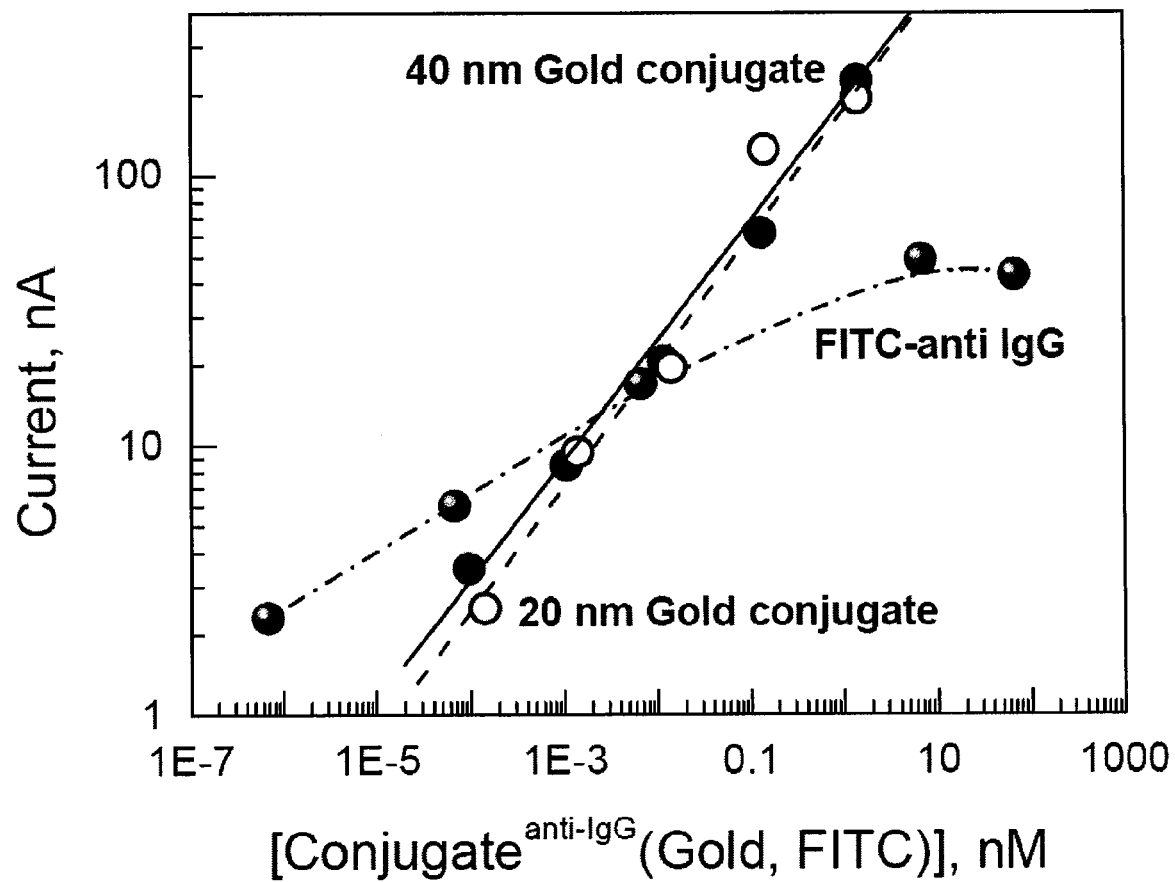
FIG. 10 shows the dependencies of the current, induced by the 473 nm laser in SiF-IgG slides, upon concentration of anti-IgG conjugates (20 nm and 40 nm Gold, or FITC).
Figure 11:
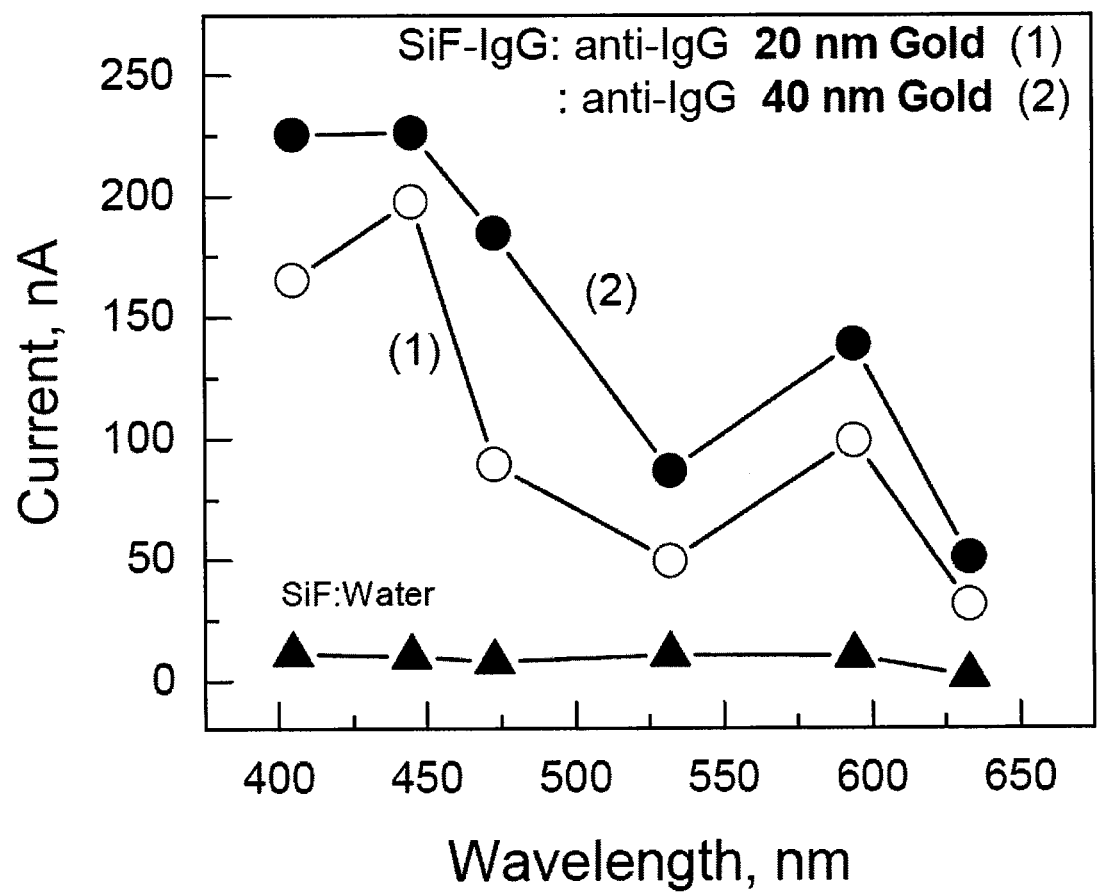
FIG. 11 shows the dependence of the current in SiF-IgG slides, coated with 20 nm and 40 nm. Gold conjugates anti-IgG, upon the wavelength of excitation. Laser powers were normalized to ≈45 mW.

Other Labels Besides Fluorophores can Cause Induced Current:

In addition to Fluorescent species, using non-fluorescent species have been considered as labels to induce current in metals. Nanoparticles such as those comprised of gold, silver, copper, platinum, also work, as shown in FIGS. 8-11. FIG. 8 shows the simple assay constructed using both 20 and 40 nm gold colloids labeled to an antibody, which binds to immobilized antigen on SiFs coated surface. The plasmon absorption spectra of the antibody gold conjugate is shown in FIG. 8. When excited with a 473 nm laser line, current is induced in the SiFs, as shown in FIG. 9. The current is gated with the on-off gating of the laser source, demonstrating that the effect is due to light on the assay substrate which has been incubated with gold-colloid labeled antibody. Remarkably, the induced current is more significant than the current induced by fluorophores in the same assay system, FIG. 10. This is due to the fact, that a bigger dipole moment is observed with the colloid label as compared to a fluorophore label at the same excitation wavelength. Interestingly, and similar to fluorophores, the wavelength dependence of the current is a function of the absorption spectra of both the colloid labels as well as the Sifs (Silver Island Films) themselves, FIG. 11.

Figure 12:
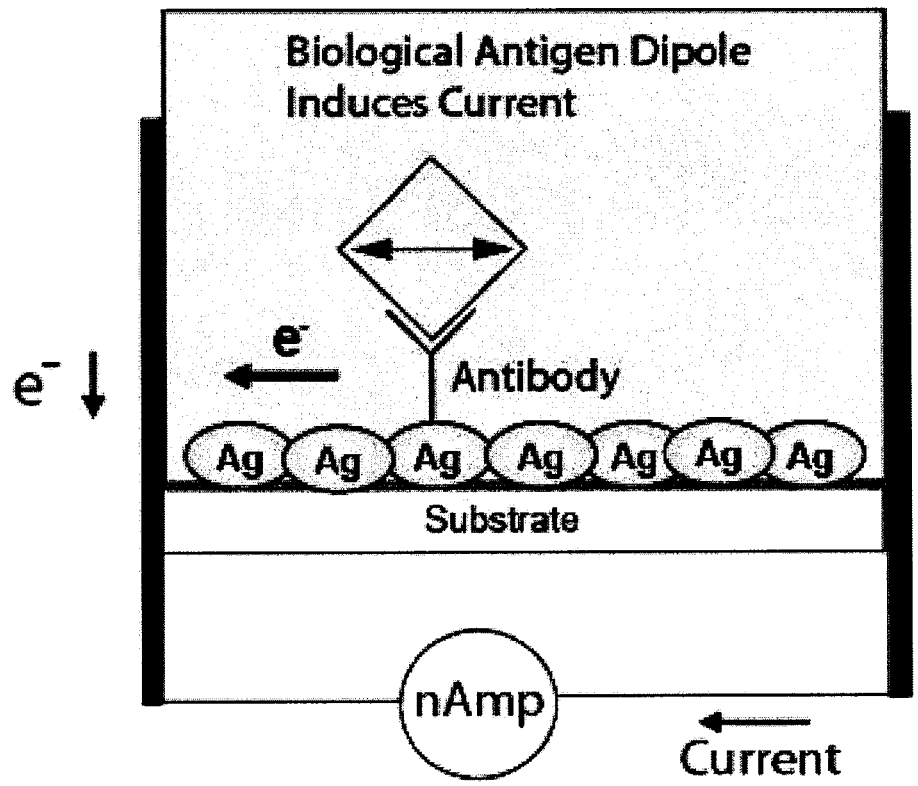
FIG. 12 shows the use of an antibody to detect a binding antigen wherein the binding antigen exhibits a dipole moment and induces dipole in the metallic particles thereby generating a current flow.
Figure 13:
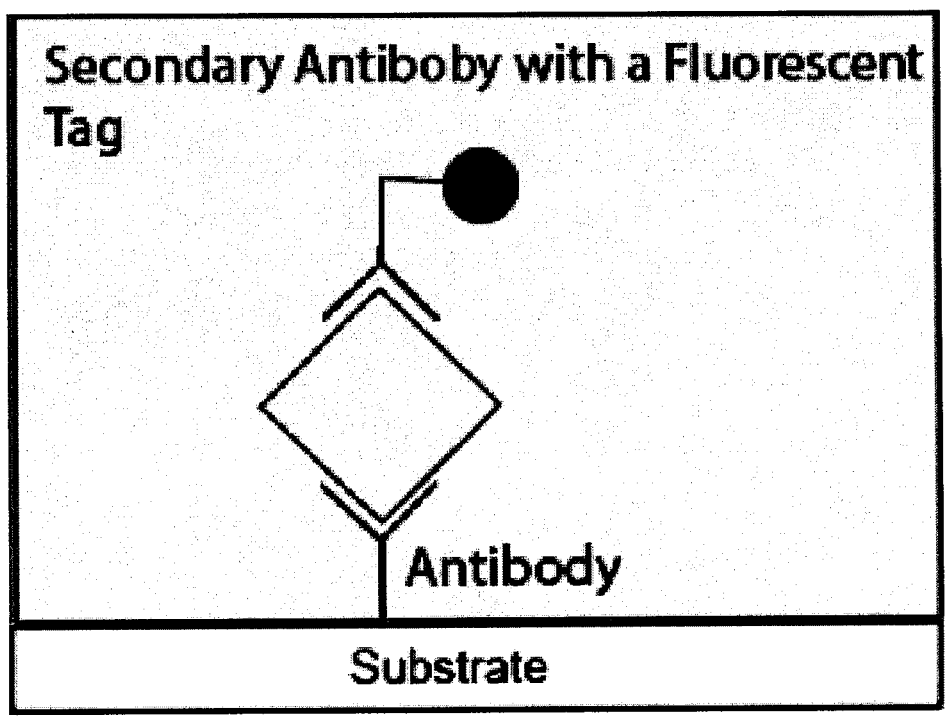
FIG. 13 shows the use of two antibodies wherein one captures the target antigen and the other provides for a fluorophore tag that upon excitation causes an induce dipole in the metallic material.

FIGS. 12 and 13 show the use of an antibody that has a dipole moment and has the ability to induce mirror dipole in the metallic particles. Notably many antigens only allow for a single antibody to bind to them so fluorescence is difficult to use for detection of these species. However, antibodies can be bound to surfaces for the capture of such antigens that has a dipole moment upon excitation can induce a dipole in the metallic material and thus induce a current. This will be very useful for applications where only one antibody can bind an antigen. A fluorophore can also be used as shown in FIG. 13.

Applications of Plasmonics Electricity Technology:

The present invention provides for multiple uses of plasmonic electricity including:

As a direct measure of Fluorescence, phosphorescence or chemiluminescence signatures.

To provide digital read out of the above, without the need for additional analogue to digital conversion processes.

In immunoassays, as a direct measurement of surface analytes by measuring induced current and not fluorescence or another luminescence signature.

As a new class of detectors, directly converting fluorescence to electricity.

In solar powering devices, with or without fluorophores or other nanoparticle labels.

To enable immunoassays to be self powering away from a wall socket.

In multiplexed and high throughput screening applications.

As devices for converting light into electricity for electronic circuits.

In DNA assays, as a direct measure of a DNA hybridization event.

In RNA assays, to directly measure current from RNA assays, after hybridization.

In chemiluminescence assays, using Horse Radish Peroxidase substrates.

As a technology to measure distance of a fluorescence (or other dipole) from a metallic substrate.

In light emitting diode constructs.

As a technology for eliminating fluorescence detection optics in fluorescence based immunoassays, one simply measures the induced current and does not bother to measure the fluorescence using a different detector, optics and filters.

Conductive materials such as textiles used for charging or powering hand held devices, such as radios, ipods and communication devices.

Conductive textiles attached to a self cooling device or to provide for color alteration of the textile.

REFERENCES

The contents of all references cited herein are incorporated by reference herein for all purposes.

(1) Collings, F. B.; Vaidya, V. S. *Toxicology* 2008, 245, 167-174.

(2) Lalvani, A.; Meroni, P. L.; Millington, K. A.; Modolo, M. L.; Plebani, M.; Tincani, A.; Villalta, D.; Doria, A.; Ghirardello, A. *Clin Exp Rheumatol* 2008, 26, S62-66.

(3) Taipa, M. A. *Comb Chem High Throughput Screen* 2008, 11, 325-335.

(4) Enander, K.; Choulier, L.; Olsson, A. L.; Yushchenko, D. A.; Kanmert, D.; Klymchenko, A. S.; Demchenko, A. P.; Mely, Y.; Altschuh, D. *Bioconjug Chem* 2008.

(5) Schultz, E.; Galland, R.; Du Bouetiez, D.; Flahaut, T.; Planat-Chretien, A.; Lesbre, F.; Hoang, A.; Volland, H.; Perraut, F. *Biosens Bioelectron* 2008, 23, 987-994.

(6) Matveeva, E.; Gryczynski, Z.; Gryczynski, I.; Malicka, J.; Lakowicz, J. R. *Analytical Chemistry* 2004, 76, 6287-6292.

(7) Matveeva, E.; Malicka, J.; Gryczynski, I.; Gryczynski, Z.; Lakowicz, J. R. *Biochem Biophys Res Commun* 2004, 313, 721-726.

(8) Aslan, K.; Gryczynski, I.; Malicka, J.; Matveeva, E.; Lakowicz, J. R.; Geddes, C. D. *Current Opinion in Biotechnology* 2005, 16, 55-62.

(9) Aslan, K.; Lakowicz, J. R.; Szmacinski, H.; Geddes, C. D. *Journal of Fluorescence* 2005, 15, 37-40.

(10) Geddes, C. D.; Lakowicz, J. R. *Journal of Fluorescence* 2002, 12, 121-129.

(11) Aslan, K.; Geddes, C. D. *Analytical Chemistry* 2005, 77, 8057-8067.

(12) Aslan, K.; Zhang, Y.; Hibbs, S.; Baillie, L.; Previte, M. J.; Geddes, C. D. *Analyst* 2007, 132, 1130-1138.

(13) Aslan, K.; Holley, P.; Geddes, C. D. *Journal of Immunological Methods* 2006, 312, 137-147.
(14) Thornycroft, L. H.; Barnaby, S. W. *Min. Proc. Inst. Chem. Eng*, 1895, 122 51-69.
(15) Suslick, K. S. *Science* 1990, 247, 1439-1445.
(16) Gould, R. K.; Coakley, W. T.; Grundy, M. A. *Ultrasonics* 1992, 30, 239-244.
(17) Suslick, K. S.; Flannigan, D. J. *Annu Rev Phys Chem* 2008, 59, 659-683.
(18) Neppiras, E. A. *Phys. Rep.* 1980, 61, 159-251.
(19) Aslan, K.; Leonenko, Z.; Lakowicz, J. R.; Geddes, C. D. *Journal of Fluorescence* 2005, 15, 643-654.
(20) Lofas, S.; Malmqvist, M.; Ronnberg, I.; Stenberg, E.; Liedberg, B.; Lundstrom, I. *Sensors and Actuators B-Chemical* 1991, 5, 79-84.

That which is claimed is:

1. A system for generating electrical current, the system comprising:
    a substrate comprising a metallic material positioned on the substrate, wherein the metallic material is shaped as particles, nanostructures, island or colloids;
    a set of electrically conductive electrodes communicatively contacting at least two of the metallic particles positioned thereon;
    an electricity storage device or a current reading device communicatively connected to at least one electrode;
    an electromagnetic energy source;
    an intrinsic or extrinsic fluorophore positioned near the metallic material, wherein excitation of the fluorophore by electromagnetic energy induces a mirror dipole in the metallic material causing plasmonic current flow for storage in the storage device or directing to the current reading device.

2. The system of claim 1, wherein the metallic material is selected from the group consisting of silver, gold, platinum, zinc, aluminum, indium, palladium, rhodium iron, nickel and copper.

3. The system of claim 1, wherein the electrodes are communicatively connected to the current reading device.

4. The system of claim 1, wherein the substrate includes glass, quartz, or a polymeric material.

5. The system of claim 1, wherein the electromagnetic energy source is positioned a distance from the first or second electrode to increase current to be detected by the current reading device.

6. The system of claim 1, wherein the mirror dipole is enhanced by a predetermined proximity to the metallic material.

7. The system of claim 6, wherein the predetermined proximity to the metallic material is from about 10 nm to 50 nm.

8. The system of claim 1, wherein the plasmonic current flow is proportional to amount of binding fluorophores.

9. The system of claim 1, wherein the wherein the metallic material is at least partially covered with a polar solvent or a dipolar aprotic solvent.

10. An assay detection method comprising:
    providing a conductive metallic material on a substrate; wherein the conductive metallic material is shaped as a non-continuous film, particles, nanostructures, island or colloids and wherein the substrate has a first end and an opposing second end;
    communicatively contacting the first and second end of the substrate and at least some of the metallic particles positioned thereon to a first and second electrode, wherein the first and second electrodes are communicatively connected to a current reading device;
    introducing at least one biomolecule for disposing near the conductive metallic material, wherein the biomolecule is capable of inducing a mirror dipole in the metallic material and such dipole is enhanced by a predetermined proximity to the metallic material;
    applying electromagnetic energy from an electromagnetic energy source to excite the biomolecule and inducing a mirror dipole in the metallic material causing plasmonic current flow, and
    measuring the plasmonic current flow by the current flow detector.

11. The assay detection method of claim 10, wherein the metallic material is selected from the group consisting of silver, gold, platinum, zinc, aluminum, indium, palladium, rhodium iron, nickel and copper.

12. The assay detection method of claim 10, wherein the substrate includes glass, quartz, or a polymeric material.

13. The assay detection method of claim 10, wherein the biomolecule comprises a fluorescing component that has the ability to fluoresce when contacted with radiation in the range from UV to IR.

14. The assay detection method of claim 10, wherein the assay system is used for hybridization assays, resonance energy transfer assays, polarization/anisotropy based assays, chemiluminescence based assays, luminescence based assays, enzyme-linked immunosorbent assays.

15. The assay detection method of claim 10, wherein the mirror dipole is enhanced by a predetermined proximity to the metallic material.

16. The assay detection method of claim 15, wherein the predetermined proximity to the metallic material is from about 10 nm to 50 nm.

17. The assay detection method of claim 10, wherein the plasmonic current flow is proportional to binding amount of fluorophores.

18. A method of metal-enhanced fluorescence sensing, comprising:
    applying a conductive metallic material to a surface used in a detection system, wherein the surface includes glass, quartz, or a polymeric material, wherein the surface has a first and second end, wherein the first and second end and at least some of the metallic material is communicatively connected to a first and second electrodes with a current measuring device positioned therebetween;
    introducing a polar solution containing at least one biomolecule for disposing near the conductive metallic surface, wherein the biomolecule is capable of excitation causing either a dipole moment or fluorescing;
    exciting the biomolecule with an electromagnetic source to cause the dipole moment or fluorescing and whereby such excitement induces a dipole in the metallic material causing plasmonic current flow;
    measuring the plasmonic current flow with the current reading device.

19. An assay method comprising:
    providing at least one vessel or container; wherein a first and second electrode are positioned within the vessel or communicatively connected thereto;
    introducing metallic nanostructures into the vessel, wherein the vessel includes a polar solution, wherein the metallic nanostructures can be free in solution or connected to a surface of the vessel;

introducing a molecule that exhibits dipole activity upon excitation and disposing such molecule near the metallic nanostructures, wherein the metallic nanostructure is positioned a predetermined proximity to the metallic nanostructures to induce a mirror dipole in the metallic nanostructures; and measuring the current flow.

* * * * *